US006635791B1

United States Patent
Magne-Drisch et al.

(10) Patent No.: US 6,635,791 B1
(45) Date of Patent: Oct. 21, 2003

(54) PROCESS FOR PRETREATING A CATALYST BASED ON AN EUO ZEOLITE UNDER SEVERE CONDITIONS

(75) Inventors: Julia Magne-Drisch, Vilette de Vienne (FR); Jean-François Joly, Lyons (FR); Elisabeth Merlen, Rueil-Malmaison (FR); Fabio Alario, Neuilly sur Seine (FR)

(73) Assignee: Institut Francais de Petrole, Rueil-Malmaison (FR)

( * ) Notice: Subject to any disclaimer, the term of this patent is extended or adjusted under 35 U.S.C. 154(b) by 0 days.

(21) Appl. No.: 09/598,483

(22) Filed: Jun. 22, 2000

(30) Foreign Application Priority Data

Jun. 22, 1999 (FR) .............................. 99 07965

(51) Int. Cl.$^7$ ................................ B01J 29/06
(52) U.S. Cl. ................... 585/481; 585/482; 502/60; 502/64; 502/66; 502/85; 502/74
(58) Field of Search ............... 585/481, 482; 502/64, 66, 74, 85, 60

(56) References Cited

U.S. PATENT DOCUMENTS

| | | | |
|---|---|---|---|
| 4,158,676 A | * | 6/1979 | Smith et al. |
| 4,202,996 A | * | 5/1980 | Hilfman |
| 4,977,117 A | * | 12/1990 | Berrebi et al. |
| 5,321,184 A | | 6/1994 | Low et al. ................ 585/481 |
| 5,817,907 A | * | 10/1998 | Benazzi et al. |
| 6,057,486 A | * | 5/2000 | Merlen et al. |
| 6,191,331 B1 | * | 2/2001 | Boldingh ................ 585/470 |

FOREIGN PATENT DOCUMENTS

EP    0 740 957    11/1996

* cited by examiner

*Primary Examiner*—Tom Dunn
*Assistant Examiner*—Christina Ildebrando
(74) *Attorney, Agent, or Firm*—Millen, White, Zelano & Branigan, P.C.

(57) ABSTRACT

The present invention concerns a process for pretreating a catalyst used in hydrocarbon conversion processes, comprising the following steps:

a) pretreating a catalyst containing at least one zeolite with structure type EUO and at least one hydrodehydrogenating metal in the presence of a hydrocarbon feed, at a temperature such that a catalyst comprising carbon is obtained;

b) then treating the hydrocarbon feed and the catalyst at a temperature which is lower than the temperature applied in step a).

The invention also concerns an activated catalyst and its use in a process for isomerizing aromatic compounds containing 8 carbon atoms.

21 Claims, No Drawings

PROCESS FOR PRETREATING A CATALYST BASED ON AN EUO ZEOLITE UNDER SEVERE CONDITIONS

FIELD OF THE INVENTION

The present invention relates to a process for pretreating a hydrocarbon conversion catalyst based on an EUO zeolite. The present invention also relates to the activated catalyst obtained and to its use in particular in the field of processes for isomerising aromatic compounds containing 8 carbon atoms.

PRIOR ART

The catalyst activated using the process of the invention can be used for isomerising aromatic compounds containing 8 carbon atoms. In known processes for isomerising aromatic compounds containing eight carbon atoms, a feed which is generally low in para-xylene with respect to the thermodynamic equilibrium of the mixture (i.e., in which the amount of para-xylene is substantially lower than that of the mixture at thermodynamic equilibrium at the temperature under consideration, this mixture comprising at least one compound selected from the group formed by meta-xylene, ortho-xylene, para-xylene and ethylbenzene), and generally rich in ethylbenzene with respect to this same mixture at thermodynamic equilibrium, is introduced into a reactor containing at least one catalyst, under suitable pressure and temperature conditions to obtain from the reactor outlet a composition of C8 aromatic compounds which is as close as possible to the composition of said mixture at thermodynamic equilibrium at the temperature of the reactor.

The para-xylene and optionally meta-xylene or ortho-xylene, which are the desired isomers as they are of great importance in particular for the synthetic fibre industry, are then separated from this mixture.

However, there are a number of problems associated with isomerising C8 aromatic compounds, caused by secondary reactions. Thus in addition to the principal isomerisation reaction, hydrogenation reactions are observed, such as hydrogenation of aromatic compounds to naphthenes, and naphthene ring opening reactions which lead to the formation of paraffins containing at most the same number of carbon atoms per molecule as the naphthenes from which they are formed. Cracking reactions are also observed, such as paraffin cracking which leads to the formation of light paraffins, typically containing three to five carbon atoms per molecule, also dismutation and transalkylation reactions which lead to the production of benzene, toluene, aromatic compounds containing nine carbon atoms and heavier aromatic compounds. All together, those secondary reactions are highly deleterious to the yields of the desired products and depend on the catalyst used for the C8 aromatic compound isomerisation reaction.

The skilled person is well aware that in certain catalytic processes, activation and/or selectivisation procedures have to be carried out on the catalyst to optimise the catalyst performance.

As an example, in the case of a catalyst containing a metal from group VIII of the periodic table, pretreating the catalyst with hydrogen sulphide ($H_2S$) is well known. The sulphur contained in the hydrogen sulphide molecule fixes itself to the metal and endows it with improved catalytic properties.

The Applicant's French patent application FR 98.04651 describes a process for activating a C8 aromatic compound isomerisation catalyst by sulphurisation and passivation with ammonia. International patent application WO-A-92/13046 describes an activation process comprising passivating a hydrocarbon catalyst based on a Y zeolite with ammonia. U.S. Pat. No. 5,321,184 describes a process for activating a C8 aromatic compound isomerisation catalyst based on pentasil zeolite by pretreatment under particular conditions.

SUMMARY OF THE INVENTION

The present invention provides a process for pretreating a catalyst used in hydrocarbon conversion processes, comprising the following steps:
a) pretreating a catalyst containing at least one zeolite with structure type EUO and at least one hydrodehydrogenating metal in the presence of a hydrocarbon feed, at a temperature such that a catalyst comprising carbon is obtained;
b) then treating the hydrocarbon feed and the catalyst at a temperature which is lower than the temperature applied in step a).

The present invention also concerns the activated catalyst obtained and the use of the activated catalyst in a process for isomerising a feed comprising xylenes and ethylbenzene.

IMPORTANCE OF THE INVENTION

The pretreatment of the invention can activate the catalyst by coating the active sites with a layer of carbon. In accordance with the invention, the catalyst comprises at least one zeolite with structure type EUO and at least one hydrodehydrogenating metal from the periodic table, and the layer of carbon deposited can attenuate the activity of the metallic and acidic sites, so that when using said catalyst in isomerising aromatic C8 compounds, the loss of aromatic C8 compounds by secondary side reactions of dismutation, transalkylation, hydrogenation and cracking can be reduced, while the selectivity is improved and good ethylbenzene conversion is retained. Further, the use of the process of the invention also comprising sulphurisation and optionally also comprising passivation with ammonia enables the catalyst to be used at lower temperatures and at higher HSVs (weight of feed/weight of catalyst/hour).

DESCRIPTION

The present invention concerns a process for pretreating a catalyst for converting hydrocarbon feeds comprising at least one EUO zeolite and at least one hydrodehydrogenating metal from the periodic table by applying severe temperature conditions when starting off the hydrocarbon conversion process, for a duration sufficient to deposit a certain quantity of carbon on the catalyst, preferably at least 0.1% by weight of carbon with respect to the total catalyst weight, and more preferably at least 0.3%. Following this treatment, the catalyst continues to be brought into contact with the hydrocarbon feed to be converted but under less severe temperature conditions than those applied during the pretreatment.

Further, in a particular implementation of the invention, the pretreatment step can comprise using a particular pressure. Thus, preferably, the pressure applied in step a) is higher than the pressure applied in step b) for the same hydrogen/hydrocarbon ratio.

In this particular implementation, step a) is then characterized in that at least one parameter selected from temperature and pressure is at a value such that the P, T set adopted leads to more favourable conditions for the formation of carbon compared with the conditions used in step b) during which the hydrocarbon conversion reaction proper is carried out.

Pretreatment step a) is carried out for a period of 5 to 120 hours, preferably 20 to 96 hours, the second step b) of the reaction proper being initiated after this first step.

Thus, for example, step a) can be applied at a temperature which is at least 20° C. higher than the temperature of step b), preferably at least 30° C. higher.

Further, the pressure can be varied. Thus, for example, step a) can be carried out at a pressure which is equal to or higher than the pressure of step b), preferably at least 0.3 MPa higher than the pressure in step b), under identical $H_2$/HC ratio conditions.

In one implementation of the invention, the catalyst is sulphurised. The catalyst is sulphurised using a sulphur compound, for example hydrogen sulphide or a hydrogen sulphide precursor. The catalyst is sulphurised before the pretreatment of the invention, without the feed and can, for example, be carried out before introducing said catalyst into the reactor, the catalyst then being termed a "pre-sulphurised catalyst". It can also be carried out using a catalyst which is already in place in the reactor.

In general, before sulphurisation, the compound of the hydrodehydrogenating metal contained in the catalyst is reduced. This pre-sulphurisation step can be carried out with pure hydrogen sulphide or with a precursor, preferably an organic precursor, of hydrogen sulphide which is then decomposed in the reactor.

Non limiting examples of sulphur-containing organic compounds which can be used in the sulphurisation step of the present invention are alkyl sulphide compounds, aryl sulphide compounds and alkylaryl sulphide compounds. Examples are butylethylsulphide, diallylsulphide, dibutylsulphide, dipropylsulphide, dimethyldisulphide (DMDS), thiophene, dimethylthiophene and ethylthiophene.

The catalyst sulphurisation step is normally carried out in a neutral or reducing atmosphere at a temperature of about 20° C. to 500° C., preferably about 200° C. to 400° C., at an absolute pressure of about 0.1 to 5 MPa, preferably about 0.3 to 3 MPa, and with a volume of gas (inert or reducing) per volume of catalyst per hour (HSV) of about 50 $h^{-1}$ to 600 $h^{1-}$, preferably about 100 $h^{-1}$ to 200 $h^{-1}$.

The inert gas is usually nitrogen and the reducing gas is usually hydrogen, most often substantially pure hydrogen.

In a further implementation of the process of the invention, the catalyst is passivated with ammonia. Passivation can be carried out before or after the sulphurisation step and these steps preferably take place before the pretreatment. Preferably, the sulphurisation step is carried out before the passivation step. These two, sulphurisation and passivation, steps can be carried out before or after introducing the catalyst into the reactor. Preferably, the passivation step in the presence of ammonia is carried out when the catalyst is already in place in the reactor and thus simultaneously with the pretreatment under severe temperature conditions and possibly severe pressure conditions.

Ammonia passivation is usually carried out in two stages: injecting a quantity of at least a certain amount of ammonia, in the form of gaseous $NH_3$, or in the form of at least one ammonia precursor, then continuous injection of ammonia in the form of gaseous $NH_3$ or in the form of at least one ammonia precursor on introducing the feed to be converted, and preferably at the same time as catalyst activation.

Preferably, the first injection is carried out with gaseous $NH_3$ and the second injection is carried out with at least one ammonia precursor.

The ammonia precursors which can be used in the present invention are all compounds which are known to the skilled person which, in the presence of hydrogen, decompose to ammonia which is fixed on the catalyst. Compounds which can be used which can be cited include aliphatic amines such as n-butylamine.

Further, the catalyst can be reduced and reduction is carried out in the presence of hydrogen, preferably more than 90 mole % pure. The reduction temperature is about 300° C. to 550° C., preferably about 400° C. to 520° C. The total pressure is in the range from atmospheric pressure to 3 MPa, preferably about 0.5 to 2 MPa. The duration of the reduction step is normally about 1 to 40 hours, pressure about 1 to 8 hours. The hydrogen flow rate (addition of fresh hydrogen and hydrogen recycled from the reactor outlet to the reactor inlet) is about 0.1 l/h/g to 100 l/h/g of catalyst.

The activated catalyst of the process of the present invention comprises at least one EUO zeolite, i.e., EU-1, TPZ-3 and ZSM-50 zeolites.

EU-1 zeolite with structure type EUO, which has already been described in the prior art, has a unidimensional microporous network with a pore diameter of 4.1×5.7 Å (1 Å=1 Angstrom=1×10$^{-10}$ m) ("Atlas of Zeolite Structure Types", W. M. Meier and D. H. Olson, 4$^{th}$ edition, 1996). Further, N. A. Briscoe et al. have disclosed in an article in the review Zeolites (1988, 8, 74) that these unidimensional channels have lateral pockets with a depth of 8.1 Å and a diameter of 6.8×5.8 Å. The mode of synthesis of EU-1 zeolite and its physico-chemical characteristics have been described in European patent EP-B1-0 042 226. U.S. Pat. No. 4,640,829 concerns ZSM-50 zeolite, which has structure type EUO according to the "Atlas of Zeolite Structure Types", W. M. Meier and D. H. Olsen, 4$^{th}$ edition, 1996. EP-A1-0 051 318 deals with TPZ-3 zeolite which has structure type EUO according to "Atlas of Zeolite Structure Types", W. M. Meier and D. H. Olson, 4$^{th}$ edition, 1996.

The zeolite with structure type EUO is at least partially in its acid form, and comprises silicon and at least one element T selected from the group formed by aluminium, iron, gallium and boron, preferably aluminium, with a global Si/T atomic ratio of more than 5.

The catalyst also comprises at least one matrix which comprises at least one compound selected from the group formed by clays, magnesia, aluminas, silicas, titanium oxide, boron oxide, zirconia, aluminium phosphates, titanium phosphates, zirconium phospates and silica-aluminas. Preferably, the matrix is alumina.

The catalyst comprises at least one hydrodehydrogenating element from the periodic table, preferably selected from group VIII metals and group VIB metals selected from palladium, platinum, nickel, iron, cobalt, chromium, manganese, tungsten, vanadium and molybdenum and can also optionally contain at least one metal selected from metals from groups IIIA and IVA, preferably selected from tin an indium.

The catalyst comprises, by weight with respect to the total catalyst mass:
  1% to 90% of at least one zeolite with structure type EUO, preferably 3% to 60%, more preferably 4% to 40%;
  0.01% to 2% by weight of at least one hydrodehydrogenating metal, preferably 0.05% to 1%;
  optionally, 0.01% to 2% of at least one additional metal selected from groups IIIA and IVA of the periodic table, preferably 0.05% to 1%;

optionally, sulphur;

a binder making up the complement to 100% of the catalyst.

In a preferred implementation of the invention, a catalyst comprising a zeolite with structure type EUO is used wherein the crystal size is less than 5 micrometres ($\mu$m), normally less than 0.5 $\mu$m and usually less than 0.2 $\mu$m. These crystals or crystallites are normally arranged as aggregates with a grain size such that the value of Dv,90 is less than or equal to 500 $\mu$m, normally less than 400 $\mu$m, usually less than 200 $\mu$m and preferably less than 50 $\mu$m. The aggregate size is determined by laser diffraction granulometry. This measurement is made on the zeolite powder suspended in water. After an initial measurement, the suspension is subjected to ultrasound for thirty seconds then a new measurement is made. The ultrasound used is characterized by a power of 50 W and a frequency of 50 kHz. This procedure is repeated until the result no longer changes (±5%). The size distribution of the aggregates defined by volume is calculated from the light signals collected by the detectors and using the Fraunhofer theory. Dv,X is defined as the diameter of the equivalent sphere such that the size of X% by volume of aggregates is less than said diameter. These characteristics are obtained directly during synthesis of the zeolite and/or by any method enabling the aggregate size to be reduced, such as post-synthesis grinding or suitable mixing before forming.

Further, the hydrodehydrogenating metal dispersion of the activated catalyst of the present invention is preferably in the range 50% to 100%, more preferably in the range 60% to 100% and still more preferably in the range 70% to 100%; the macroscopic distribution coefficient of said hydrodehydrogenating metal is in the range 0.7 to 1.3, preferably in the range 0.8 to 1.2. Preferably, the catalyst is formed into beads or extrudates and its strength is such that its bed crushing strength is more than 0.7 MPa.

The invention also concerns the use of the catalyst in a process for isomerising a feed comprising at least one xylene isomer selected from para-xylene, ortho-xylene and meta-xylene, and ethylbenzene.

In this implementation of the invention, the catalyst pretreatment process is carried out in the same reaction zone as the isomerisation reaction for the xylenes and ethylbenzene.

Thus in the case where the activated catalyst is used in a process for isomerising aromatic compounds containing 8 carbon atoms, the activated catalyst is characterized in that it comprises carbon and in that pretreatment step a) is carried out under severe temperature and pressure conditions. Thus, for example, the pretreatment of step a) is carried out at a temperature in the range 400° C. to 500° C., radical at a temperature in the range 410° C. to 450° C. Further, the pressure can be varied. As an example, a total pressure in the range 1 to 2 MPa can be applied during step a), preferably in the range 1.2 to 1.8 MPa.

The isomerisation process is then carried out during step b) using any method which is known to the skilled person. As an example, the isomerisation reaction temperature during step b) is about 300° C. to 410° C., preferably about 320° C. to 400° C. and more preferably about 350° C. to 400° C.; the partial pressure of hydrogen is about 0.3 to 1.5 MPa, preferably about 0.4 to 1.2 MPa; the total pressure is about 0.45 to 1.9 MPa, preferably about 0.6 to 1.5 MPa; the HSV (weight of feed/weight of catalyst/hour) is about 0.25 to 15 $h^{-1}$, preferably about 1 to 10 $h^{-1}$, and more preferably about 2 to 7 $h^{-1}$.

In this implementation of the invention, the catalyst contains at least one metal from group VIII of the periodic table, preferably platinum or palladium.

In a preferred implementation of the isomerisation process of the present invention, along with the feed to be isomerised and the hydrogen required for the reaction, at least one compound with a boiling point in the range about 80° C. to 135° C. is introduced, more particularly at least one compound selected from the group formed by paraffins containing eight carbon atoms per molecule, benzene, toluene and naphthenes containing eight carbon atoms.

This or these compounds are added to the feed to be isomerised as a recycle, in the form of fresh compounds or in the form of a mixture of recycled and fresh compounds in quantities such that the percentages by weight of added compounds with respect to the total feed entering the reactor are normally as follows:

the percentage by weight of paraffins containing eight carbon atoms, in the optional case when they are added to the feed, is about 0.1% to 10%, preferably about 0.2% to 2%;

the percentage by weight of naphthenes containing eight carbon atoms, in the optional case when they are added to the feed, is about 0.5% to 15%, preferably about 2% to 8%;

the percentage by weight of toluene, in the optional case when it is added to the feed, is about 0.1% to 10%, preferably about 0.2% to 5%;

the percentage by weight of benzene, in the optional case when it is added to the feed, is about 0.1% to 10%, preferably about 0.2% to 2%.

The percentage by weight of the total mass of added compounds, when adding a plurality of compounds, is normally about 0.1% to 20% by weight, preferably about 2% to 15% by weight with respect to the total feed entering the isomerisation zone.

The following examples illustrate the invention without in any way limiting its scope.

The following abbreviations are used in the examples in the present description: "C1–C8 paraffins" for paraffins containing 1 to 8 carbon atoms; "C5–C9 naphthenes" for naphthenes containing 5 to 9 carbon atoms; and "C9–C10 aromatic compounds" for aromatic compounds containing 9 and 10 carbon atoms.

EXAMPLES

Example 1

In Accordance with the Invention

The catalyst used in this Example was prepared as follows.

The starting material was a zeolite with structure type EUO, EU-1 zeolite, as synthesised, comprising an organic template, silicon and aluminium, with a global Si/Al atomic ratio of 13.6, and a sodium content of about 1.5% with respect to the weight of dry EU-1 zeolite, corresponding to an atomic ratio Na/Al of 0.6.

This EU-1 zeolite first underwent dry calcining at 550° C. in a stream of air for 6 hours. The solid obtained then underwent three ion exchange steps in a 10 N $NH_4NO_3$ solution at about 100° C. for 4 hours per exchange step.

After these treatments, the EU-1 zeolite in its $NH_4$ form had a global Si/Al atomic ratio of 18.3, and a sodium content with respect to the weight of dry EU-1 zeolite of 50 ppm by weight.

The EU-1 zeolite was then formed by extrusion with an alumina gel to obtain, after drying and calcining in dry air, support S1 constituted by extrudates 1.4 mm in diameter which contained 10% by weight of EU-1 zeolite in its H form and 90% of alumina.

Support S1 obtained underwent anion exchange with hexachloroplatinic acid in the presence of a competing agent (hydrochloric acid), to introduce platinum into the catalyst. The moist solid was then dried at 120° C. for 12 hours and calcined in a dry air stream at 500° C. for 1 hour.

The catalyst obtained contained 10.0% by weight of EU-1 zeolite in its H form, 89.7% of alumina and 0.29% of platinum.

After charging the catalyst, drying and reducing the metal compound contained in the catalyst at 450° C., a sulphurisation step was carried out using hydrogen sulphide (H$_2$S) at a pressure of 16 bars absolute.

To carry out this sulphurisation, a quantity of H$_2$S equal to 0.1% by weight with respect to the catalyst mass was introduced, the temperature then being 380° C.

After injecting the H$_2$S, the reactor was kept at 380° C. for 1 hour with a hydrogen recycle—without a hydrogen makeup. Then the temperature of the reactor was raised to 390° C., the temperature increase being made slowly over one hour. It remained at 390° C. for two hours.

The feed (hydrocarbon mixture) was then injected at 425° C. and 15 bars absolute pressure and these operating conditions were applied for 72 hours. During this catalyst pretreatment period, samples were regularly removed (every 2 hours) to follow the evolution of the catalytic performance. The duration of the pretreatment period was estimated by monitoring the paraffin losses. After 72 hours, these losses had stabilised, catalyst pretreatment was halted and the operational conditions were adjusted.

The catalyst performance was evaluated under the following conditions:

| | |
|---|---|
| Temperature | 380° C. |
| Pressure | 9 bar |
| H$_2$/HC | 4 |

The inlet/outlet compositions of the unit are shown in the following table.

| Compounds | Feed (wt %) | Effluent (wt %) |
|---|---|---|
| C1–C9 paraffins | 0.50 | 1.46 |
| C5 to C9 naphthenes | 1.14 | 8.85 |
| Benzene | 0.00 | 0.08 |
| Toluene | 0.52 | 0.66 |
| Ethylbenzene | 12.88 | 7.65 |
| Para-xylene | 3.65 | 19.23 |
| Meta-xylene | 60.81 | 42.67 |
| Ortho-xylene | 20.48 | 18.78 |
| C9–C10 aromatic compounds | 0.02 | 0.58 |

The proportion of para-xylene with respect to the three xylene isomers was 23.83% by weight for a global yield of aromatic compounds+naphthenes containing 8 carbon atoms of 97.94%, i.e., the loss of C8 aromatic compounds in the form of paraffins, naphthenes and aromatic compounds other than those containing 8 carbon atoms was 2.06% by weight.

Example 2

Not in Accordance with the Invention

The same catalyst as that described in the preceding example was charged, dried, reduced and sulphurised using the procedures described above. Then the same feed was injected at 380° C. and at 9 bars.

After stabilising the catalyst performance, the catalytic performance was evaluated under the same conditions as above.

The inlet/outlet compositions of the unit are shown in the following table:

| Compounds | Feed (wt %) | Effluent (wt %) |
|---|---|---|
| C1–C9 paraffins | 0.50 | 1.84 |
| C5 to C9 naphthenes | 1.14 | 9.26 |
| Benzene | 0.00 | 0.09 |
| Toluene | 0.52 | 0.78 |
| Ethylbenzene | 12.88 | 7.56 |
| Para-xylene | 3.65 | 18.92 |
| Meta-xylene | 60.81 | 42.33 |
| Ortho-xylene | 20.48 | 18.41 |
| C9–C10 aromatic compounds | 0.02 | 0.81 |

The proportion of para-xylene with respect to the three xylene isomers was 23.75% by weight for a global yield of aromatic compounds+naphthenes containing 8 carbon atoms of 97.11%, i.e., the loss of C8 aromatic compounds in the form of paraffins, naphthenes and aromatic compounds other than those containing 8 carbon atoms was 2.89% by weight.

For the same approximate equilibrium of para-xylene, the losses were higher (2.89% as opposed to 2.06%) in the case of the catalyst which had not undergone initial pretreatment.

What is claimed is:

1. A process for pretreating a catalyst used in an isomerization process of a feed that contains at least one aromatic compound having 8 carbon atoms, the process comprising the following steps:

a) pretreating a catalyst containing at least one zeolite with structure type EUO and at least one hydrodehydrogenating metal while converting a hydrocarbon feed that contains at least one aromatic compound containing 8 carbon atoms, at a temperature whereby a catalyst comprising carbon is obtained for a period of 72 to 120 hours;

b) then continuing converting the hydrocarbon feed with the catalyst at a temperature which is lower than the temperature applied in a).

2. A process according to claim 1, in which during pretreatment step a), at least 0.1% by weight of carbon with respect to the total catalyst weight is deposited.

3. A process according to claim 1, in which the temperature applied in step a) is at least 20° C. higher than the temperature applied in step b).

4. A process according to claim 1, in which in addition, the pressure applied in step a) is greater than or equal to the pressure applied in step b).

5. A process according to claim 1, in which the catalyst is sulphurised.

6. A process according to claim 1, in which the catalyst is passivated with ammonia.

7. A process according to claim 1, in which passivation with ammonia is carried out in two stages, the first stage comprising injecting ammonia in the form of NE$_3$ gas or in the form of a compound which is an ammonia precursor; and a second stage comprising continuously injecting ammonia in the form of NH$_3$ gas or in the form of a compound which is an ammonia precursor when introducing the feed to be converted.

8. A process according to claim 1, in which the zeolite in the catalyst is EU-1 zeolite with structure type EUO, this zeolite containing silicon and at least one element T selected from the group formed by aluminium, iron, gallium and boron, such that the global Si/T atomic ratio is more than 5, said zeolite further being at least partially in the acid form, and at least one hydrodehydrogenating metal selected from metals from group VIB and VIII of the periodic table.

9. A process according to claim 1, in which the treated catalyst also comprises at least one matrix.

10. A process according to claim 1, in which the treated catalyst further comprises at least one metal selected from the group formed by metals from groups IIIA and IVA of the periodic table.

11. A process according to claim 1, in which the crystal size of the zeolite with structure type EUO is less than 5 micrometres ($\mu$m).

12. A process according to claim 1, in which the EUO zeolite crystals are arranged in aggregates with a grain size such that the value of Dv,90 is 500 $\mu$m or less.

13. A process according to claim 1, in which the hydrodehydrogenating metal dispersion in the catalyst is in the range 50% to 100%.

14. A process according to claim 1, in which the macroscopic distribution coefficient of the hydrodehydrogenating metal is in the range 0.7 to 1.3.

15. A process according to claim 1, in which the strength of the catalysts is such that the bed crushing strength is more than 0.7 MPa.

16. A process according to claim 1, in which the catalyst comprises at least one group VIII metal selected from platinum and palladium.

17. A process according to claim 1, in which the temperature of step a) is in the range 400° C. to 500° C.

18. A process according to claim 17, in which during step b), the temperature is about 300° C. to 420° C., with a partial pressure of hydrogen of about 0.3 MPa to 1.5 MPa at a total pressure of about 0.45 MPa to 1.9 MPa and at a HSV of about 0.25 to 15 h$^{-1}$, and the temperature of step a) is at least 20° C. higher than the temperature of step b).

19. A process according to claim 18, in which along with the feed to be isomerised, at least one compound with a boiling point of about 80° C. to 135° C. selected from the group formed by paraffins containing 8 carbon atoms, naphthenes containing 8 carbon atoms, toluene and benzene is introduced in the form of a fresh compound, in the form of a recycled compound or in the form of a mixture of fresh and recycled compounds.

20. A process for pretreating a catalyst used in an isomerization process of a feed that contains at least one aromatic compound having 8 carbon atoms, the process comprising the following steps:
  a) pretreating a catalyst containing at least one zeolite with structure type EUO and at least one hydrodehydrogenating metal while converting a hydrocarbon feed that contains at least one aromatic compound containing 8 carbon atoms, at a temperature whereby a catalyst comprising carbon is obtained for a period of 72 to 120 hours;
  b) then continuing converting the hydrocarbon feed with the catalyst at a temperature which is lower than the temperature applied in a), and at a pressure that is at least 0.3 MPa lower than the pressure applied in a).

21. A process for pretreating a catalyst used in an isomerization process of a feed that contains at least one aromatic compound having 8 carbon atoms in which the at least one aromatic compound containing 8 carbon atoms is selected from the group consisting of para-xylene, ortho-xylene, meta-xylene and ethylbenzene, the process comprising the following steps:
  a) pretreating a catalyst containing at least one zeolite with structure type EUO and at least one hydrodehydrogenating metal while converting a hydrocarbon feed that contains at least one aromatic compound containing 8 carbon atoms, at a temperature whereby a catalyst comprising carbon is obtained for a period of 72 to 120 hours;
  b) then continuing converting the hydrocarbon feed with the catalyst at a temperature which is lower than the temperature applied in a).

* * * * *